(12) United States Patent
Luider et al.

(10) Patent No.: US 9,334,519 B2
(45) Date of Patent: *May 10, 2016

(54) METHODS AND MEANS FOR CHARACTERIZING ANTIBIOTIC RESISTANCE IN MICROORGANISMS

(71) Applicant: Erasmus University Medical Center Rotterdam, Rotterdam (NL)

(72) Inventors: Theo M. Luider, Rotterdam (NL); Jeroen van Kampen, Rotterdam (NL); Alexander F. Van Belkum, Leiden (NL); Wilhelm Goessens, Hellevoetsluis (NL); Gero P. Hooff, Mannheim (DE)

(73) Assignee: Erasmus University Medical Center Rotterdam, Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/643,597

(22) Filed: Mar. 10, 2015

(65) Prior Publication Data

US 2015/0184217 A1 Jul. 2, 2015

Related U.S. Application Data

(63) Continuation of application No. 13/817,748, filed as application No. PCT/NL2010/050523 on Aug. 19, 2010.

(51) Int. Cl.
| | | |
|---|---|---|
| C12Q 1/04 | (2006.01) | |
| C12Q 1/02 | (2006.01) | |
| C12Q 1/18 | (2006.01) | |
| G01N 33/68 | (2006.01) | |
| C12Q 1/34 | (2006.01) | |

(52) U.S. Cl.
CPC .. *C12Q 1/02* (2013.01); *C12Q 1/04* (2013.01); *C12Q 1/18* (2013.01); *C12Q 1/34* (2013.01); *G01N 33/6848* (2013.01)

(58) Field of Classification Search
CPC ...................................................... C12Q 1/02
See application file for complete search history.

(56) References Cited

U.S. PATENT DOCUMENTS

| | | | |
|---|---|---|---|
| 6,120,986 | A | 9/2000 | Martin |
| 8,580,535 | B2 | 11/2013 | Gocorun et al. |
| 2005/0089947 | A1 | 4/2005 | Black et al. |
| 2008/0009029 | A1 | 1/2008 | Govorun et al. |
| 2011/0012016 | A1 | 1/2011 | Maier et al. |
| 2011/0245105 | A1 | 10/2011 | Citri |

FOREIGN PATENT DOCUMENTS

| | | |
|---|---|---|
| CN | 102033102 | 4/2011 |
| CN | 103003699 | 3/2013 |
| DE | 102006021493 | 11/2007 |
| DE | 102009033368 | 1/2011 |
| GB | 2438066 | 11/2007 |
| WO | 2010067358 | 6/2010 |

OTHER PUBLICATIONS

Liesener and Karst, "Monitoring enzymatic conversions by mass spectrometry: a critical review", Anal Bioanal Chem., 382(7), pp. 1451-1464, Aug. 2005.
Gao et al., "Novel fluorogenic substrates for imaging beta-lactamase gene expression", J Am Chem Soc., 125(37), pp. 11146-11147, Sep. 2003.
Ji et al., "Identification of Streptothricin Class Antibiotics in the Early Stage of Antibiotics Screening by Electrospray Ionization Mass Spectrometry", Journal of Antibiotics, 61(11): 660-667, 2008.
Neu, Structure-Activity Relations of New beta-Lactam Compounds in Vitro Activity Against Common Bacteria, Reviews of Infectious Diseases, vol. 5, Supplement 2, 1983.
Rathore et al., "Extending matrix-assisted laser desorption/ionization triple quadruple mass spectrometry enzyme screening assays to targets with small molecule substrates", Rapid Communications in Mass Spectrometry, 23:3293-3300, 2009.
Cohen et al., "Small molecule analysis by MALDI mass spectrometry", Anal. Bional. Chem., 2002, 373:571-586.
Affinity-purification, Thermo Scientific website, Jan. 14, 2010.
Saves et al., "Mass spectral kinetic study of acylation and deacylation during the hydrolysis of penicillins and cefotaxime by beta-lactamase TEM-1 and the G238S mutant", Biochemistry, vol. 34, No. 37, 1995, pp. 11660-11667.
Aplin et al, "Use of electrospray mass spectrometry to directly observe an acyl enzyme intermediate in beta-lactamase catalysis", Febs Letters, Elsevier, vol. 277, No. 1-2, 1990, pp. 212-214.
Fenselau et al., "Identification of Lactamase in Antibiotic-Resistant Bacillus cereus Spores", Applied and Environmental Microbiology, vol. 74, No. 3, 2007, pp. 904-906.
Keseru et al., "Identification of beta-lactamases in human and bovine isolated of *Staphylococcus aureus* strains having borderline resistance to penicillinase-resistant penicilians (PRPs) with proteomic methods", Veterinary Microbiology, Elsevier, vol. 147, No. 1-2, 2011, pp. 96-102.
Dargis et al., "Use of biotinylated beta-lactams and chemluminescence for studying of penicillin-binding proteins in bacteria", Antimicrobial Agents and Chemotherapy, May 1994, pp. 973-980.

(Continued)

*Primary Examiner* — Albert Navarro
(74) *Attorney, Agent, or Firm* — O'Shea Getz P.C.

(57) ABSTRACT

The present invention relates to a method for characterizing the antibiotic resistance of a microorganism, the method comprising the steps of (a) providing a reference mass spectrum of an antimicrobial compound, its enzymatic modification product, its molecular target, or of a substrate compound of a its modifying enzyme; (b) exposing a microorganism, a cell lysate thereof, or a growth medium supernatant thereof, to the antimicrobial compound or the substrate compound in aqueous liquid to thereby provide an exposed sample; (c) acquiring a mass spectrum of the exposed sample; (d) comparing the mass spectrum acquired in step c) with the reference mass spectrum of step (a), and (e) determining from the comparison whether modification of the antimicrobial compound, its modification product or its molecular target or of the substrate has occurred following the exposure, and establishing that the microorganism is potentially resistant to the antimicrobial compound when the modification is observed.

11 Claims, No Drawings

(56) References Cited

OTHER PUBLICATIONS

Ohkawa et al., "The Isolation Frequency of B-Lactamase-Producing Fungus from Acute Uncomplicated Cystitis Patient", Proceedings of Urinology, Nov. 1987, vol. 33, No. 77, p. 1800-1805.

Niu et al., "SanJ, an ATP-dependent picolinate-CoA ligase, catalyzes the conversion of picolinate to picolinate-CoA during nikkomycin biosynthesis in Streptomyces ansochromogenes", Metab. Eng., May 2006, vol. 8, No. 3, p. 183-195.

Welling et al., "Determination of enzyme activity by high-performance liquid chromatography", J. Chromatogr. B. Biomed. Appl., Sep. 1994, vol. 659, No. 1-2, p. 209-225.

Lewis et al., "A point mutation leads to altered product specificity in beta-lactamase catalysis", Proc. Natl. Acad. Sci. USA, Jan. 1997, vol. 94, No. 2, p. 443-447.

Yazawa K et al: "Inactivation of Kanamycin a by Phosphorylation in Pathogenic Nocardia", Microbiology and Immunology, vol. 35, No. 1, 1991, pp. 39-48, XP009144264.

Mosher et al: "Inactivation of Chloramphenicol by 0-Phosphorylation: A Novel Resistance Mechanism in Streptomyces venezuelae ISP5230, A Chloramphenicol Producer" Journal of Biological Chemistry, vol. 270, No. 45, 1995, pp. 27000-27006.

Ikryannikova et al: "A Maldi TOF MS-Based Minisequencing Method for Rapid Detection of TEM-Type Extended-Spectrum Beta-Lactamases in Clinical Strains of Enterobacteriaceae", Jouranl of Microbiological Methods, vol. 75, No. 3, Dec. 1, 2008, pp. 385-391.

Chinese Office Action dated Mar. 13, 2015.

METHODS AND MEANS FOR CHARACTERIZING ANTIBIOTIC RESISTANCE IN MICROORGANISMS

PRIORITY INFORMATION

This patent application is a continuation U.S. patent application Ser. No. 13/817,748 filed on Feb. 19, 2013, which claims priority from PCT patent application PCT/NL2010/050523 filed Aug. 19, 2010, which is hereby incorporated by reference.

FIELD OF INVENTION

The present invention is in the field of bacterial diagnostics and relates in particular to a method for characterizing the antibiotic resistance of a microorganism, to a kit of parts for performing the method of the invention and to a system for characterizing the antibiotic resistance of a microorganism comprising a mass spectrometric device and sample preparation materials for performing the method of the invention.

BACKGROUND OF THE INVENTION

Antibiotic resistance is the ability of a microorganism to withstand the effects of an antibiotic. This resistance develops through genetic mutation and plasmid exchange between microorganisms. Already, antibiotic resistance is having a major impact on medicine that will only increase in the coming years.

One group of the opportunistic microorganisms that gain renewed interest for exhibiting antibiotic resistance are the Enterobacteriaceae. These bacterial species (including for example *Klebsiella* spp and *Escherichia coli*) comprise opportunistic pathogens that have i.a. been associated with urinary tract infections, septicaemia, respiratory tract infections and diarrhea. Resistance of these species to third generation cephalosporins such as oxyimino beta-lactams has been known for 30 years but an exponential increase in resistance has since been recorded. Strains gain their resistance by producing so-called extended-spectrum beta-lactamases (ESBLs), which are Molecular Class A beta-lactamases, capable of inactivating third-generation cephalosporins (ceftazidime, cefotaxime, and cefpodoxime) as well as monobactams (aztreonam) ESBLs are derivatives of common beta-lactamases (e.g. TEM and SHV beta-lactamases) that have undergone one or more amino acid substitutions near the active site of the enzyme, thus increasing their affinity for and hydrolytic activity against third generation cephalosporins and monobactams. Extensive use of newer generation cephalosporins drives the evolution of an increasing range of new ESBLs. ESBLs are encoded by transferable conjugative plasmids that are responsible for the dissemination of resistance to other members of gram negative bacteria.

ESBLs are distinguished into more than 450 types based on their physical properties and are variably inhibited by clavulanate, sulbactam and tazobactam, a property which has been used to detect them in the laboratory. Currently, only phenotypic ESBL detection tests are used in the clinical microbiology laboratory. Molecular (genotypic) tests are under development. A problem with molecular tests is, however, the lack of a 100% correlation between the genotype and the phenotype. Hence, the predictive value of molecular testing for any bacterial phenotype, including ESBL producing bacteria, is limited.

In general, the current phenotypic laboratory tests are sensitive and specific as compared to ESBL genotypic confirmatory tests. All phenotypic ESBL detection tests rely on the same principle: the tests assess variation in the inhibition of bacterial growth in the presence of beta-lactam antibiotics or combinations of beta-lactam antibiotics and beta-lactamase inhibitors. Various manual tests and automated platforms are commercially available for performing these phenotypic tests. The manual tests use disks or strips impregnated with beta-lactam antibiotics or combinations of beta-lactam antibiotics and beta-lactamase inhibitors. The impregnated material is placed on solid media that is pre-inoculated with a bacterial suspension of known density. Following overnight incubation, growth inhibition is determined visually and can be quantified on the basis of the diameter of inhibition zones. The automated systems are also based on measurement of bacterial growth in the presence of panels of beta-lactam antibiotics or combinations of beta-lactam antibiotics and beta-lactamase inhibitors at different concentrations. Results of such systems are obtained after 4 h-18 h.

There is presently a need for means and methods that are capable of diagnosing ESBL producing bacteria more rapidly. There is also a need for an ESBL detection test that can be used in the clinical microbiology laboratory to characterize the ESBL enzymes in terms of enzyme kinetics in order to track evolutionary trends and evaluate and predict the effective dosage in antibiotic therapy. Preferably, such means find wider applicability in characterizing antibiotic resistance in microorganisms in general.

SUMMARY OF THE INVENTION

The present invention now provides means and methods for rapid diagnosis of antibiotic modifying enzyme-producing microorganisms, in particular (in preferred embodiments) microorganisms that produce ESBL. The present invention further provides means and methods for characterizing the antibiotic modifying enzymes themselves. Such characterization may lead to an earlier detection of novel types of resistance.

In a first aspect, the present invention provides a method for characterizing the antibiotic resistance of a microorganism, the method comprising the steps of:
a) providing a reference mass spectrum of an antimicrobial compound, its enzymatic modification product, its molecular target, or of a substrate compound of a its modifying enzyme;
b) exposing a microorganism, a cell lysate thereof, or a growth medium supernatant thereof, to the antimicrobial compound or the substrate compound in aqueous liquid to thereby provide an exposed sample;
c) acquiring a mass spectrum of the exposed sample;
d) comparing the mass spectrum acquired in step c) with the reference mass spectrum of step a), and
e) determining from the comparison whether modification of the antimicrobial compound, its modification product or of the substrate or whether overproduction of its molecular target has occurred following the exposure, and establishing that the microorganism is potentially resistant to the antimicrobial compound when the modification is observed.

In a preferred embodiment of the method, the modification comprises enzymatic inactivation or enzymatic degradation of the antimicrobial compound, and/or methylation or overproduction of its molecular target. More preferably, the enzymatic degradation is due to degradation by a beta-lactamase. In such instance, the antimicrobial compound may be a beta lactam antibiotic or any other beta-lactamase substrate. Hence, in another preferred embodiment of the method, the antimicrobial compound may be replaced by a substrate compound of an enzyme that modifies antimicrobial compounds. In other preferred embodiments the antimicrobial compound is a beta-lactam antibiotic, preferably selected from the group consisting of penicillins, cephalosporins, cephamycins, and carbapenems, more preferable selected from the group consisting of ceftazidime, cefotaxime, ceftriaxone, cefpodoxime, and aztreonam.

It is clear that, depending on the mechanism of antibiotic resistance, also the molecular target of the antimicrobial compound (such as for instance folate) may be overproduced, which results in resistance to folate antagonists. Target overproduction may be detected by using internal standards and observing that the ratio of target/internal standard is increased. Suitable internal standards may be nucleic acids such as DNA.

Further, again depending on the mechanism of antibiotic resistance, also the methylation of the molecular target of the antimicrobial compound (such as for instance nucleic acid) may be detected.

In yet another preferred embodiment of a method of the invention, the method is performed by exposing the microorganism to multiple antimicrobial compounds simultaneously, thereby characterizing the antibiotic resistance of the microorganism for multiple antibiotic compounds.

In yet another preferred embodiment of a method of the invention, the enzymatic inactivation or enzymatic degradation of the antimicrobial compound is brought about by a beta-lactamase. In particularly preferred embodiments, the beta-lactamase enzyme may be selected from the group consisting of cephalosporinases (including extended spectrum cephalosporinases), penicillinases, carbenicillinases, cloxacillinases and carbapenemases.

In still a further preferred embodiment of a method of the invention, the beta lactamase enzyme is an extended-spectrum beta lactamase (ESBL).

In still a further preferred embodiment of the method, the microorganism is a suspected ESBL-producing microorganism, preferably a Gram-negative bacterium, more preferably a Gram-negative bacterium selected from *Klebsiella pneumoniae, Escherichia coli, Klebsiella oxytoca* and *Proteus mirabilis*.

The samples used in aspects of the invention comprise microorganisms or lysis products thereof. The samples of microorganisms may be samples of cultures of microorganisms. Such cultures need not be pure cultures. Alternatively, also fractions of culture media or direct clinical materials can be a source of the sample.

In yet another preferred embodiment of the method, the method is part of a method for characterization of an antibiotic modifying enzyme of a microorganism, preferably the antibiotic modifying enzyme is an extended-spectrum beta lactamase (ESBL) enzyme. In a particularly preferred embodiment, the method of the invention is part of a method for characterization of an extended-spectrum beta lactamase (ESBL) enzyme.

Preferably, the method for characterization of the enzyme according to the invention comprises the determination of the rate of modification, preferably degradation, of the antimicrobial compound or the substrate compound with or without the presence of specific enzymatic inhibitors and/or the rate of production of the enzymatic modification product of the compound or substrate or the rate of overproduction of the molecular target of the compound to thereby determine the Michaelis-Menten (Km) constant and maximum reaction rate (Vmax) for the enzyme.

In yet another preferred embodiment of the method, the mass spectra are acquired using MALDI triple-quadrupole Mass Spectrometry.

In yet another preferred embodiment of the method, the exposed sample is an exposed crude cell lysate of the microorganism.

In yet another preferred embodiment of the method, the method further comprises the step of quantifying the microorganism. Preferably, the microorganism is quantified by quantifying in the samples one or more structural biomolecules or metabolites derived from the microorganism. In preferred embodiments, the structural biomolecules or metabolites are selected from the group consisting of nucleic acids, preferably (genomic) DNA. DNA is present as a single molecule inside the cell and can be quantified using for instance PCR- and/or DNA probing mediated technologies.

In another aspect, the present invention provides a kit-of-parts for characterizing the beta-lactam antibiotic resistance of a microorganism comprising:
  a) a lysis buffer for lysing a microorganism;
  b) at least one antimicrobial compound or a substrate of an antimicrobial compound-modifying enzyme, and
  c) a MALDI matrix material,
preferably the kit of parts further comprising:
  d) a carrier carrying the at least one antimicrobial compound or substrate, wherein the carrier is optionally in the fours of a disposable mass spectrometric sample support.

In yet another aspect, the present invention provides a system adapted for characterizing the beta-lactam antibiotic resistance of a microorganism by a method of the invention as described above, the system comprising one or more of the following:
  at least one antimicrobial compound or a substrate of an antimicrobial compound-modifying enzyme;
  a container for exposing a microorganism, a cell lysate thereof, or a growth medium supernatant thereof, to the at least one antimicrobial compound in aqueous liquid, preferably wherein the at least one substrate compound is provided in the container;
  a lysis buffer for lysing the microorganism;
  a MALDI matrix material;
  a mass spectrometry device;
  a reference mass spectrum of an antimicrobial compound, its enzymatic modification product, its molecular target, or of a substrate compound of a its modifying enzyme, and
  a mass spectrometric sample support,
optionally further comprising
  an automated pipetor for liquid handling;
  a computer program comprising computer program code means for performing all the steps of the method of the invention as described above when the program is run on a computer including for instance algorithms for results interpretation, interface software and/or expert system software.

The invention in another aspect provides a computer program comprising computer program code means for performing all the steps of the method of the invention as described above when the program is run on a computer.

In another aspect the invention provides a computer program product comprising computer program code means stored on a computer readable medium for performing the method of the invention as described when the program product is run on a computer.

These and other objects, features and advantages of the present invention will become more apparent in light of the following detailed description of preferred embodiments thereof, as illustrated in the accompanying drawings.

DETAILED DESCRIPTION OF THE INVENTION

Definitions

The terms "antibiotic" and "antimicrobial compound" are used interchangeably herein and are used herein to describe a compound or composition which decreases the viability of a microorganism, or which inhibits the growth or reproduction of a microorganism "Inhibits the growth or reproduction" means increasing the generation cycle time by at least 2-fold, preferably at least 10-fold, more preferably at least 100-fold, and most preferably indefinitely, as in total cell death. As used in this disclosure, an antibiotic is further intended to include an antibacterial, bacteriostatic, or bactericidal agent. Non-limiting examples of antibiotics useful in aspect of the invention include penicillins, cephalosporins, aminoglycosides, sulfonamides, macrolides, tetracyclins, lincosamides, quinolones, chloramphenicol, glycopeptides, metronidazole, rifampin, isoniazid, spectinomycin, folate inhibitors, sulfamethoxazole, and others.

The term "beta-lactam antibiotic" is used to designate compounds with antibiotic properties containing a beta-lactam functionality. A beta-lactam ring (β-lactam) is a cyclic amide comprising a heteroatomic ring structure, consisting of three carbon atoms and one nitrogen atom. Non-limiting examples of beta-lactam antibiotics useful in aspects of the invention include penicillins, cephalosporins, cephamycins, penems, carbapenems, and monobactams. Beta-lactam antibiotics are effective (in the absence of resistance) against a wide range of bacterial infections. The term "beta-lactam antibiotic" as used herein is considered to include any antibiotic undergoing mass or structural changes upon inactivation by an antibiotic resistant microorganism, provided the mass or structural change can be detected by mass spectrometry.

The term "third generation cephalosporin" refers to such compounds including, but not limited to cefixime, ceftazidime, cefotaxim, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, and oxacephem.

The term "beta-lactamase" means an enzyme (EC 3.5.2.6) produced by a microorganism, preferably a bacterium, that has the ability to hydrolyze the beta-lactam ring of beta-lactam antibiotics. Such enzymes are often classified into 4 major classes (Classes A, B, C, and D) according to the so-called Ambler classification scheme, based principally on protein homology. Examples of beta-lactamases include cephalosporinase, penicillinase, carbenicillinase, cloxacilanase, carbapenemase, and ceftazidimase. It is meant that the term includes "normal" beta-lactamase, extended-spectrum beta lactamase (ESBL), as well as AmpC beta-lactamase. Preferred beta-lactameses in aspects of the present invention are group A and D beta-lactamase enzymes according to the Ambler classification or are beta-lactam enzymes belonging to group 2 according to the Bush classification (Bush et al. 1995. Antimicrob Agents Chemother. 39: 1211-33). Ambler class A antibiotics are the classic active-site serine beta-lactamases and class D are a specific group of serine beta-lactamases that have little sequence similarity with the class A beta-lactamases and are familiarly known as the OXA (oxacillinase) group. Also preferred is metallo-carbapenemase.

The term "extended-spectrum beta lactamase" (abbr. ESBL), as used herein, initially called 'extended-broad-spectrum beta-lactamase', was first coined for derivatives of TEM and SHV enzymes able to hydrolyse oxyimino-cephalosporins. These all belonged to beta-lactamase functional group 2be. Subsequently, the term has been stretched to include: (i) enzymes with spectra similar to those of TEM and SHV mutants but derived from other sources, e.g., the CTX-M and VEB types; (ii) TEM and SHV mutants with borderline ESBL activity, e.g., TEM-12; and (iii) various beta-lactamases conferring wider resistance than their parent types but not meeting the definition for group 2be, e.g., OXA derivatives and mutant AmpC types with increased activity against cefepime.

The terms "resistant" and "resistance", as used herein, refer to the phenomenon that a microorganism does not exhibit decreased viability or inhibited growth or reproduction when exposed to concentrations of the antimicrobial agent that can be attained with normal therapeutic dosage regimes in humans. It implies that an infection caused by this microorganism cannot be successfully treated with this antimicrobial agent.

The term "microorganism", as used herein, refers in particular to pathogenic microorganisms, such as bacteria, yeast, fungi and intra- or extra-cellular parasites. In preferred aspects of the present invention, the term refers to pathogenic or opportunistic bacteria. These include both Gram-positive and Gram-negative bacteria. By way of Gram-negative bacteria, mention may be made of bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia, Actinobacillus, Alcaligenes, Bordetella, Cedecea, Erwinia, Pantoea, Ralstonia, Stenotrophomonas, Xanthomonas* and *Legionella*. By way of Gram-positive bacteria, mention may be made of bacteria of the following genera: *Enterococcus, Streptococcus, Staphylococcus, Bacillus, Listeria, Clostridium, Gardnerella, Kocuria, Lactococcus, Leuconostoc, Micrococcus, Mycobacteria* and *Corynebacteria*. By way of yeasts and fungi, mention may be made of yeasts of the following genera: *Candida, Cryptococcus, Saccharomyces* and *Trichosporon*.

The term "mass spectrum", as used herein, refers to a plot having molecular mass or a function thereof (e.g., mass-to-charge ratio (m/z), ion mass, etc.) as the independent variable. The dependent variable is typically a quantitative measure, such as abundance, relative abundance, intensity, concentration, number of ions, number of molecules, number of atoms, counts/millivolt, counts, etc. For example, in the context of ions, a mass spectrum typically presents mass-to-charge ratio (m/z) as the independent variable, where m is the mass of the ion species and z is the charge of the ion species, and the dependent variable is most commonly an abundance of each molecular ion and/or its fragment ions. The term "ion" means an atom or a group of atoms that has acquired a net electric charge by gaining or losing one or more electrons or gaining or losing one or more protons. An ion can be formed in numerous manners, including by breaking up a molecule of a gas under the action of an electric current, of ultraviolet and certain other rays, and/or of high temperatures.

The term "reference mass spectrum", as used herein, refers to a control mass spectrum intended for comparative analysis.

The term "substrate compound of a modifying enzyme", as used herein, refers to any compound (antibiotic or not) that can be hydrolyzed by an antibiotic-modifying enzyme. The enzymatic modification of the substrate will give rise to a reaction product with a different mass-to-charge ratio (or mass spectrum) than the original substrate compound. The reaction product, in the case that the enzymatic conversion is a degradation, may be referred to herein as the "degradation product".

The term "modifying enzyme", as used herein refers broadly to an antimicrobial compound-modifying enzyme, such as for instance a beta-lactamase.

"Modification" as used herein refers to a chemical or physical (preferably chemical) alteration of the antimicrobial compound which renders the compound inactive with respect to its antimicrobial activity. Modification may include degradation, which refers to the deletion of chemical moieties from the compound molecule resulting in a lower molecular mass, optionally in combination with an altered mass-to-charge ratio. Alternatively, modification may include substitution or addition of chemical moieties on the compound molecule, thereby inactivating the compound with respect to its antimicrobial activity, which mode of modification provides the molecule with an altered mass, optionally in combination with an altered mass-to-charge ratio.

The term "cell lysate" as used herein refers to cell suspensions or fractions thereof, obtained by disruption or lysing of the cells. The crude cell lysate contains all proteins, glycoproteins, polysaccharides, lipids, and nucleic acids. The cell lysate in aspects of the present invention may comprise whole cells, but will essentially consist of parts of cells or any fraction or mixtures thereof obtained after a lysis step. Cell lysate solutions, however, can include, without limitation, a solution of lysed cells that is treated such that selected molecules are removed or rendered inactive. It follows that this solution remains substantially "crude" with respect to most purified cellular constituents. For example, a cell lysate can be a solution of lysed cells that is treated with an agent that inactivates or removes polymerase inhibitors. In addition, a cell lysate can be a solution of lysed cells that is treated with an anti-coagulant. Any method can be used to lyse cells in a cellular sample. For example, osmotic shock, sonication, heating, physical disruption, microwave treatment, and enzymatic and/or alkaline lysis are methods that can be used to lyse cells.

The term "growth medium", as used herein, refers to a medium comprising all the elements necessary for the expression of a metabolism and/or for the growth of microorganisms. The growth medium may be solid, semi-solid or liquid. The growth medium may comprise one or more elements in combination, such as amino acids, peptones, carbohydrates, nucleotides, minerals, vitamins, active molecules such as antibiotics, enzymes, surfactants, buffers, phosphate salts, ammonium salts, sodium salts, metal salts, one or more substrates enabling the detection of an enzyme activity, etc.

The term "supernatant", as used herein, refers to the liquid suspension remaining when cells grown in a liquid medium (e.g., a liquid broth) are removed by centrifugation, filtration, sedimentation, or other means well known in the art, and containing dissolved and suspended material.

The terms "matrix material" and "MALDI matrix material", as used herein, are interchangeable and refer to a compound, whether in solution or solid, which may be used to form a matrix for use in MALDI mass spectrometry. For MALDI, the analyte must be embedded in a large excess of molecules which are well-absorbing at the wavelength at which the laser emits. These matrix molecules are generally small, organic compounds, mainly acids. Appropriate matrix materials for each type of laser used in MALDI are well known in the art and the term "MALDI matrix material" will be clearly understood by one of skill in the art. Without limiting the present invention, examples of commonly used matrix materials include sinapinic acid (SA), α-cyano-4-hydroxycinnamic acid (HCCA), 2,5-dihydroxybenzoic acid (DHB), 7-hydroxy-4-(trifluoromethyl)coumarin (HFMC), 3-Hydroxy Picolinic Acid (3-HPA), 5-(trifluoro-methyl) uracil, caffeic acid, succinic acid, anthranilic acid, 3-aminopyrazine-2-carboxylic acid, tetrakis(pentafluorfenyl)porfyrine and ferulic acid. Matrices are suitably dissolved in acetonitrile/water/formic acid (500:500:1; v/v/v), or other suitable ratio's depending on the matrix used.

The term "sample", as used herein, refers to a substance that contains or is suspected of containing an analyte, such as a microorganism or beta lactamase to be characterized, or a beta-lactamase substrate or its beta-lactamase degradation product. A sample useful in a method of the invention can be a liquid or solid, can be dissolved or suspended in a liquid, can be in an emulsion or gel, and can be bound to or absorbed onto a material. A sample can be a biological sample, environmental sample, experimental sample, diagnostic sample, or any other type of sample that contains or is suspected to contain the analyte of interest. As such, a sample can be, or can contain, an organism, organ, tissue, cell, bodily fluid, biopsy sample, or fraction thereof. A sample useful in a method of the invention can be any material that is suspected to contain analytes, such as substrates of beta-lactamases and ESBLs. In a biological context, a sample can include biological fluids, whole organisms, organs, tissues, cells, microorganisms, culture supernatants, subcellular organelles, protein complexes, individual proteins, recombinant proteins, fusion proteins, viruses, viral particles, peptides and amino acids.

The term "sample support", as used herein, refers to all supports that are suitable to receive a sample for MALDI MS analysis. Commonly used are 10×10 stainless steel target plates (Perseptive Biosystems, Framingham, Mass., USA), if appropriate the target plates can be hydrophobically coated.

The term "Michaelis-Menten constant", often referred to as "Km", as used herein, refers to the substrate concentration at which the rate of enzymatic reaction is half its maximum. The term "maximum reaction rate", often referred to as "Vmax", as used herein, refers to the maximum rate of an enzymatic reaction at saturating substrate concentrations. Michaelis-Menten kinetics describe the rate of production of molecules produced by enzymatic chemical reactions. To determine the maximum rate of an enzymatic reaction, the substrate concentration is increased until a constant rate of product formation is achieved. This is the 'maximum velocity' (Vmax) of the enzyme. In this state, enzyme active sites are saturated with substrate. Since the substrate concentration at Vmax cannot be measured exactly, enzymes can be characterized by the substrate concentration at which the rate of reaction is half its maximum. This substrate concentration is referred to as the Michaelis-Menten constant (KM). For enzyme reactions exhibiting simple Michaelis-Menten kinetics, this represents the dissociation constant (affinity for substrate) of the enzyme-substrate (ES) complex. Low values indicate high affinity.

The term "MALDI triple-quadrupole MS", as used herein, refers to a technique of matrix-assisted laser desorption/ionization wherein the mass spectrometer has three quadrupoles arranged parallel to incoming ions. The first quadrupole acts as a mass filter. The second quadrupole acts as a collision cell where selected ions are broken into fragments. The resulting fragments are scanned by the third quadrupole. Quadrupole mass analyzers use oscillating electrical fields to selectively stabilize or destabilize the paths of ions passing through a radio frequency (RF) quadrupole field. Only a single mass-to-charge ratio is passed through the system at any time, but changes to the potentials on magnetic lenses allows a wide range of m/z values to be swept rapidly, either continuously or in a succession of discrete hops. A quadrupole mass analyzer acts as a mass-selective filter.

The term "quantifying", as used herein, refers to any method for obtaining a quantitative measure. For example, quantifying a microorganism can include determining its abundance, relative abundance, intensity, concentration, and/or count, etc.

The term "structural biomolecule", as used herein, refers to any cell protein, glycoprotein, polysaccharide, lipid, nucleic acid etc the amount of which is essentially constant between individual cells of a culture of microorganisms, and which can be used to quantify those microorganisms. If DNA is used for instance, quantification can proceed via DNA amplification or the use of (MS identifiable) nucleic acid probes. Such methods for quantification may for instance use standard calibration curves wherein DNA content is plotted against cell number or another biomass parameter (such as optical density in culture or total carbon mass).

The term "metabolite", as used herein, refers to a compound generated as a result of the functioning of a biochemical reaction in a cell or organism the amount of which is essentially constant between individual cells of a culture of microorganisms, and which can be used to quantify those microorganisms.

PREFERRED EMBODIMENTS

The invention provides in a method for characterizing the antibiotic resistance of a microorganism. A first step in such a method is the provision of one or more reference mass spectra of antibiotic compounds, suitable mimetic substrates thereof, or of molecular targets of the antibiotic compound for which resistance is to be characterized. Reference spectra can be produced by using any mass spectrometric (MS) technique that is to be used in the analysis of the samples. A preferred MS technique is MALDI-MS.

A suitable beta-lactamase substrate is any beta lactam antibiotic. Alternatively, beta-lactam derivatives or mimetics may be used that induce expression of the beta-lactamase in the microorganism, and/or that are hydrolysed by enzymatic activity of the beta-lactamase. The mimetic substrates used in aspects of the invention themselves may, but need not necessarily, exhibit any antibiotic activity.

Preferably, the beta-lactamase substrate is a compound of which the beta-lactamase degradation product is readily discernable by MS, preferably such that the substrate and its degradation product have different mass-to-charge ratios.

A further step in a preferred method for characterizing the beta-lactam antibiotic resistance of a microorganism involves the exposure of a microorganism, a cell lysate thereof, or a growth medium supernatant thereof, to the substrate compound in aqueous liquid to thereby provide an exposed sample.

A suitable exposed sample may be a body fluid or body tissue sample of a subject, i.e. a human or animal subject, suspected of carrying a microorganism the beta-lactam antibiotic resistance of which is to be characterized. Suitable body fluid samples may be blood, stool or urine sample.

The exposure of the microorganism to the substrate compound may thus involve in vivo or in vitro exposure.

Exposure may in certain embodiments comprise an incubation step wherein the microorganism is incubated for a short period of time, for instance between 1-5 minutes and 1-3 hours in a solution containing the antimicrobial agents of interest. In addition, lysates of microorganisms and supernatants of microbial cultures can be used. When the specific enzymes are present, the antimicrobial agents or their mimetic substrates are modified or inactivated resulting in a different composition in elements compared to the active drug form. This leads to a change in the mass of the antimicrobial agent that can be detected by mass spectrometry.

It is an advantage of the present invention that crude cell lysates can also be used to provide an exposed sample. Hence, the microorganism that is to be characterized needs no longer be viable, nor does the exposed sample need to be purified before any beta-lactamase activity therein can be detected.

When a microorganism contains a beta-lactamase gene but does not produce the enzyme itself under the prevailing growth conditions, beta-lactamase production in that organism may be induced by culturing the microorganism in presence of a beta-lactam antibiotic or a beta-lactamase-inducing compound. Preferably, an optional step of inducing or activating beta-lactamase production takes place prior to bacterial cell lysis.

In general, the capacity of the exposed sample to modify an antibiotic compound may be detected by detecting either a decrease in the antibiotic substrate compound (or its mimetic), or an increase in the reaction product of the hydrolysis reaction between modifying enzyme and substrate compound. Hence, the beta-lactamase activity in the exposed sample may be detected by detecting either a decrease in the beta-lactamase substrate compound or an increase in the reaction product of the hydrolysis reaction between beta-lactamase and substrate compound.

Alternatively, the capacity of the exposed sample to modify an antibiotic compound may be detected by detecting a modification in the molecular target of the antibiotic compound. For instance, resistance to erythromycin, ciprofloxacin, vancomycin, methiciline and tetracycline is based on target modification, such as RNA methylation. Also these target modifications may be detected by mass spectrometry as described herein. Hence, the present invention is not limited to the detection of beta-lactamases as modifying enzymes, and hence the characterization of resistance to beta-lactams. Also other resistance to antibiotic compounds that is not based on drug modification can be characterized using the aspects of the present invention. Although beta-lacams usually inactivate the antibiotic drugs by hydrolysis, other types of enzymatic modification can also be detected and characterized using the means and methods of the present invention. For instance, aminoglycosides are modified by the addition of a phosphate moiety. Such modifications of the substrate of the modifying enzyme can also be detected by the methods of the present invention.

It is an important finding of the present inventors that the change in (quantitative amount of) reaction or target compounds can be measured very accurately by mass spectroscopy. Hence, after the incubation step, the exposed sample is prepared for mass spectrometry using generic mass spectrometry sample preparation protocols such as protein precipitation with organic solvents, solid-phase extraction (SPE), or liquid-liquid extraction (LLE). Approximately 1 µL of the prepared solution is used for the mass spectrometric analysis. In preferred embodiments of the present invention, MALDI MS is used and more preferably MALDI quadrupole MS is used. Using MALDI MS, the reaction compounds can be measured with such accuracy that exposure times (incubation periods) can be very short. Successful characterizations have been attained with an incubation time of about 5 minutes.

Maldi MS involves applying the exposed sample together with a matrix material to a mass spectrometric sample support and drying the sample on the sample support to produce a mass spectrometric sample. Suitable matrix materials are indicated herein above, and the nature of the matrix material is not particularly limiting. The preparation of the mass spectrometric sample from the exposed sample can be performed by methods known per se to one of skill in the art of mass spectrometry.

Once the sample is mounted in the mass spectrometer, the mass spectrum of the sample is acquired by standard procedures that depend on the type of equipment and MS methods used.

In a method of the invention, the step of detecting substrate or target modification (such as beta lactamase substrate degradation or RNA methylation) is performed by using MS, preferably by tandem mass spectrometry (MS-MS) or by matrix-assisted laser desorption/ionization (MALDI). Mass spectrometry provides a powerful means of determining the structure and identity of complex organic molecules, including proteins and peptides. In MS, a sample compound is bombarded with high-energy electrons causing it to fragment in a characteristic manner. The fragments, which are of varying weight and charge, are then passed through a magnetic field and separated according to their mass-to-charge ratios. The resulting characteristic fragmentation signature pattern of the sample compound (the mass spectrum) is used to identify and quantitate that compound. A typical MS procedure comprises the following steps:

1. loading of a sample onto the MS instrument, by applying the sample optionally (in case of a special form of MS called MALDI) together with a matrix on a mass spectrometric sample support and drying the sample or the mixture on the support by evaporation of the solvents.
2. ionizing the components of the sample by one of a variety of methods (e.g., by impacting them with an electron beam), which results in the formation of charged particles (ions)
3. accelerating the positive ions by an electric field
4. computating the mass-to-charge ratio (m/z) of the particles based on the details of motion of the ions as they transit through electromagnetic fields, and
5. detecting the ions, which in step 4 were sorted according to m/z.

In MALDI MS, the matrix consists of crystallized molecules, of which the three suitable examples are 3,5-dimethoxy-4-hydroxycinnamic acid (sinapinic acid), α-cyano-4-hydroxycinnamic acid (alpha-cyano or alpha-matrix) and 2,5-dihydroxybenzoic acid (DHB). The matrix solution is mixed with the exposed sample. The organic solvent allows hydrophobic molecules to dissolve into the solution, while the water allows for water-soluble (hydrophilic) molecules to do the same. This solution is spotted onto a MALDI plate or support (usually a metal plate designed for the purpose). The solvents evaporate, leaving only the recrystallized matrix, together with the sample molecules dispersed throughout the matrix crystals.

Suitable MS applications that can be used in aspects of the invention include MALDI-TOF MS mass spectrometry, MALDI-FT mass spectrometry, MALDI-FT-ICR mass spectrometry, MALDI Triple-quadrupole mass spectrometry. Using MALDI-TOF mass spectrometry, the throughput is estimated to be 1 minute per sample. Using MALDI-triple quadrupole mass spectrometry, the duration of the test can be decreased to approximately 5 seconds per sample without loss of sensitivity or specificity.

Following the acquisition of the mass spectra, the sample-derived mass spectra are compared with the reference mass spectra of the antimicrobial compound, its enzymatic modification product, its molecular target, or of a substrate compound of a its modifying enzyme in a qualitative, semi-quantitative or quantitative manner. By such comparison, the qualitative, semi-quantitative or quantitative presence of modification of the substrate or the target and/or the production of modification products can be determined.

Both the inactivated or modified antibiotic (e.g. degradation product) and intact antibiotic substrate (or the mimetic substrate), as well as the molecular target can be measured simultaneously by mass spectrometry, and the ratio of product-to-substrate can for instance be taken as a measure of the microorganism's ability to inactivate or modify the tested substrates. Alternatively or in addition, a decrease in the level of the substrate alone or an increase in the level of the product alone in the sample can be used as a measure of the antibiotic-inactivating or antibiotic-modifying ability of the microorganism. Alternatively, an increase in the level of the molecular target, or an increase in the level of the modified (resistant) target, may be taken as an indication of the microorganism's resistance. In case of characterization of antibiotic resistance against drugs involving target modification as resistance mechanism, the step of exposing a microorganism, a cell lysate thereof, or a growth medium supernatant thereof, to an antimicrobial compound in aqueous liquid will amount to the provision of a sample of the microorganism, a cell lysate thereof, or a growth medium supernatant thereof, and the detection therein of modified targets.

Hence, in one embodiment of aspects of the invention, modification of the antimicrobial substrate compound is taken as proof for the production of for instance a beta lactamase by the microorganism, and indicates that the microorganism is likely to be resistant to the beta-lactam antibiotic compounds that are inactivated, for instance by degradation, by that specific beta lactamase for which an antimicrobial substrate compound or suitable mimetic substrate was provided. In this way, the resistance of the microorganism to for instance a beta-lactam antibiotic may be characterized.

Alternatively, in another embodiment of aspects of the invention, the presence of a modification (in relative amount or in chemical composition) of the molecular target of the antimicrobial compound in the microbial cell is taken as an indication that the microorganism is likely to be resistant to the antibiotic compound of interest. In this way, the resistance of the microorganism to for instance erythromycin, ciprofloxacin, vancomycin, methiciline and tetracycline may be characterized.

In aspects described above, the invention provides in certain embodiments a method for the rapid diagnosis of microorganisms that produce enzymes that inactivate or structurally modify antimicrobial agents. The method can be used for rapid detection of ESBL activity. Especially in a hospital setting, this is highly needed because third generation cephalosporins are widely used in the empiric therapy for seriously ill patients with infections. Rapid detection of ESBL activity in a patient's sample is of importance to start as early as possible with the most appropriate antibiotic drug therapy for that patient. The methods of the present invention can be used for rapid detection of ESBL activity. Furthermore, the methods of the present invention can be applied on supernatants of microbial cultures or on microorganisms isolated directly from a patient's sample, e.g. after centrifugation of urine samples. In this way, it should be possible to detect ESBL activity even sooner than detection of the (cultured) bacteria themselves.

Mass spectrometry has not been used to detect enzymatic inactivation or chemical modification of antibiotics by monitoring the decrease in substrate intensity and/or the increase in product intensity. Furthermore, mass spectrometry has not been used to study enzyme activity in complex samples such as lysed microorganisms. More in particular, the specific detection and characterization of ESBL enzymes by MS has never been reported before.

A diagnostic method for rapid detection of ESBL activity suitably comprises the liberation from the microorganisms of the beta lactamase enzymes that inhibit the antimicrobials by lysing the sample using a lysis reagent. Subsequently, these lysates may be transferred, preferably using an automated pipetor, into a multiwell strip, such as the ATB™ or Rapidec™ strips, which strips contain wells with reagents for performing different test reactions based on different antimicrobial compounds. Some of the wells contain a certain amount of one or several beta lactamase substrates, for instance in a dried or immobilized (glued) form. Some of the wells could also contains one or several internal standard(s) for easing quantification. Some wells could also be used as control without substrates for self-degradation of the antimicrobial compounds.

Following the transfer into the wells, and the incubation therein for a short period of time as indicated herein, the exposed sample of each well may suitably be put on a MALDI plate or any other MS support. In the case of MALDI, a suitable matrix material is added to the support. Thereafter, the mass spectra are acquired. Spectral analysis is suitably performed using dedicated analysis algorithms. The spectra as obtained from the exposed sample are then compared with reference spectra using computer software in order to determine the presence of degradation of the substrate for each well. In case of degradation, dedicated software may provide the test results in a report, which report may include, for instance: (1) the identity (species name) of the microorganism (which identification may be brought about by reference tests, optionally available in the same or a parallel teststrip), (2) a list of tested antimicrobials as provided in the multiwall test strip, (3) a list of antimicrobials inhibited or degraded by the microorganism, (4) the resistance mechanism(s) supposed to be responsible of antimicrobial inhibition, (5) dedicated interpretation comments with regards to the results.

Alternatively, the step of exposing a microorganism, a cell lysate thereof, or a growth medium supernatant thereof, to the substrate compound in aqueous liquid (to thereby provide an exposed sample), may be performed on the mass spectrometric sample support. Upon allowing the optionally present beta lactam enzymes to degrade the substrate compound of a beta-lactamase enzyme on the sample support the MALDI matrix may be added to the exposed sample directly.

A method of the present invention can be performed using complex samples, including crude cell lysates or patient samples. The method allows for the precise assessment of molecules in the size range of antimicrobial agents (normally between 200 and 1000 daltons) and can suitably be used to determine the activity of antibiotic-inactivating or antibiotic-modifying enzyme, for instance using antimicrobial drugs as substrates.

A method of the present invention can also be used as ESBL confirmatory test. In most clinical microbiology laboratories bacteria are first screened for the ESBL phenotype and then the ESBL phenotype is confirmed using a separate ESBL phenotypic confirmatory test. Aspects of the present invention can be used to confirm the ESBL phenotype in bacteria. The potential advantage of a method of the present invention over current phenotypic tests is that the method proposed herein not only works with bacterial suspensions but also with lysates of bacteria. The use of bacterial lysates neutralizes the potential bias due to resistance based on other mechanisms, in particular decreased influx and increased efflux of drugs. Use of bacterial lysates is incompatible with current phenotypic ESBL confirmatory tests, because these tests rely on bacterial growth.

A method of the present invention can also be used as high throughput screening method for new beta-lactamase inhibitors in the pharmaceutical industry. Currently, the beta-lactamase inhibitors clavulanic acid and tazobactam are combined with amoxicillin and piperacillin respectively to overcome the problem of beta-lactamase producing bacteria. The clavulanic acid or tazobactam inhibit the activity of the beta-lactamases while the amoxicillin or piperacillin kill the bacteria. Considering the growing problem of ESBL, the pharmaceutical industry needs tools to screen for novel compounds that inhibit ESBLs. The present invention is highly suited for this purpose.

EXAMPLES

We have detected beta-lactamase activity in crude lysates of *E. coli* producing CTX-M-1 and CTX-M-9 and in *K. pneumoniae* producing SHV-2 using benzylpenicillin as substrate. We were able to monitor the enzyme kinetics of pure penicillinase (from *B. cereus*) using benzylpenicillin as substrate.

Although the present invention has been illustrated and described with respect to several preferred embodiments thereof, various changes, omissions and additions to the form and detail thereof, may be made therein, without departing from the spirit and scope of the invention.

What is claimed is:
1. A method for characterizing the antibiotic resistance of a microorganism, the method comprising the steps of:
   (a) providing a reference mass spectrum of a molecular target of an antimicrobial compound;
   (b) exposing the microorganism, a cell lysate thereof, or a growth medium supernatant thereof, to the antimicrobial compound in aqueous liquid to thereby provide an exposed sample;
   (c) acquiring a mass spectrum of the exposed sample;
   (d) comparing the mass spectrum acquired in step c) with the reference mass spectrum of step a), and
   (e) determining from the comparison whether modification of the molecular target has occurred following the exposure, and establishing that the microorganism is potentially resistant to the antimicrobial compound when the modification is observed.

2. The method according to claim 1, wherein the modification comprises methylation or overproduction of the molecular target.

3. The method according to claim 1, wherein the microorganism is one of *Klebsiella pneumoniae, Escherichia coli, Klebsiella oxytoca* and *Proteus mirabilis*.

4. The method according to claim 1, wherein the antimicrobial compound is a beta-lactam antibiotic.

5. The method according to claim 1, wherein after step (b) the exposed sample is applied together with a matrix material to a mass spectrometric sample support and wherein the sample is dried on the sample support to produce a mass spectrometric sample for matrix-assisted laser desorption ionization mass spectrometry (MALDI-MS).

6. The method according to claim 5, wherein the mass spectra are acquired using MALDI triple-quadrupole MS.

7. The method according to claim 1, wherein the exposed sample is an antimicrobial compound-exposed crude cell lysate of the microorganism.

8. The method according to claim 1, wherein in step (b) the microorganism is quantified by quantifying in the samples one or more structural biomolecules or metabolites derived from the microorganism, wherein the structural biomolecules or metabolites are DNA molecules.

9. The method according to claim 4, wherein the antimicrobial compound is selected from a group comprising penicillins, cephalosporins, cephamycins, and carbapenems, ceftazidime, cefotaxime, ceftriaxone, cefpodoxime, and aztreonam.

10. The method according to claim 1, wherein the mass spectrum is acquired using one of MALDI triple-quadrupole mass spectrometry, MALDI-TOF mass spectrometry and MALDI-FTICR mass spectrometry.

11. The method according to claim 1, wherein the exposed sample is a body fluid or body tissue sample of a human or animal subject suspected of carrying a microorganism.

\* \* \* \* \*

UNITED STATES PATENT AND TRADEMARK OFFICE
CERTIFICATE OF CORRECTION

| | | |
|---|---|---|
| PATENT NO. | : 9,334,519 B2 | Page 1 of 1 |
| APPLICATION NO. | : 14/643597 | |
| DATED | : May 10, 2016 | |
| INVENTOR(S) | : Luider et al. | |

It is certified that error appears in the above-identified patent and that said Letters Patent is hereby corrected as shown below:

IN THE SPECIFICATION

Column 4
Line 27, please delete "fours" and insert --form--

Signed and Sealed this
Fifth Day of July, 2016

Michelle K. Lee
*Director of the United States Patent and Trademark Office*